United States Patent

Wells

[11] Patent Number: 4,501,642
[45] Date of Patent: Feb. 26, 1985

[54] METHOD OF PAPER TENSION CONTROL TO MAINTAIN FLUTTER WITHIN A PREDETERMINED RANGE

[75] Inventor: Henry A. Wells, Oxford, Ohio

[73] Assignee: Champion International Corporation, Stamford, Conn.

[21] Appl. No.: 546,993

[22] Filed: Oct. 31, 1983

Related U.S. Application Data

[62] Division of Ser. No. 422,001, Sep. 23, 1982.

[51] Int. Cl.³ .................... D21F 7/00; G01N 21/86; G01V 9/04
[52] U.S. Cl. .................................. 162/198; 73/159; 250/561; 356/1
[58] Field of Search .............. 162/198, 263, 252, 253, 162/256, DIG. 10, 199; 73/159; 356/1, 376; 250/560, 561

[56] References Cited

U.S. PATENT DOCUMENTS

| | | | |
|---|---|---|---|
| 3,379,390 | 4/1968 | Eastcott | 250/561 |
| 3,721,376 | 3/1973 | Christian et al. | 250/561 |
| 4,160,694 | 7/1979 | Futcher | 162/256 |
| 4,174,237 | 11/1979 | Henning, Jr. | 162/256 |

Primary Examiner—Steve Alvo
Attorney, Agent, or Firm—Evelyn M. Sommer; William W. Jones

[57] ABSTRACT

Method of paper tension control to maintain the frequency and amplitude of paper flutter. A noncontacting sensor means is mounted adjacent a portion of the paper path in a paper manufacturing apparatus. The sensor means detects flutter in a paper web travelling across the paper path. The tension in the paper web can be determined from the frequency and amplitude of the flutter. By adjusting the tension in the paper web to maintain the flutter within a predetermined range of frequency and amplitude, the tension in the paper web can be maintained at a desired level.

3 Claims, 1 Drawing Figure

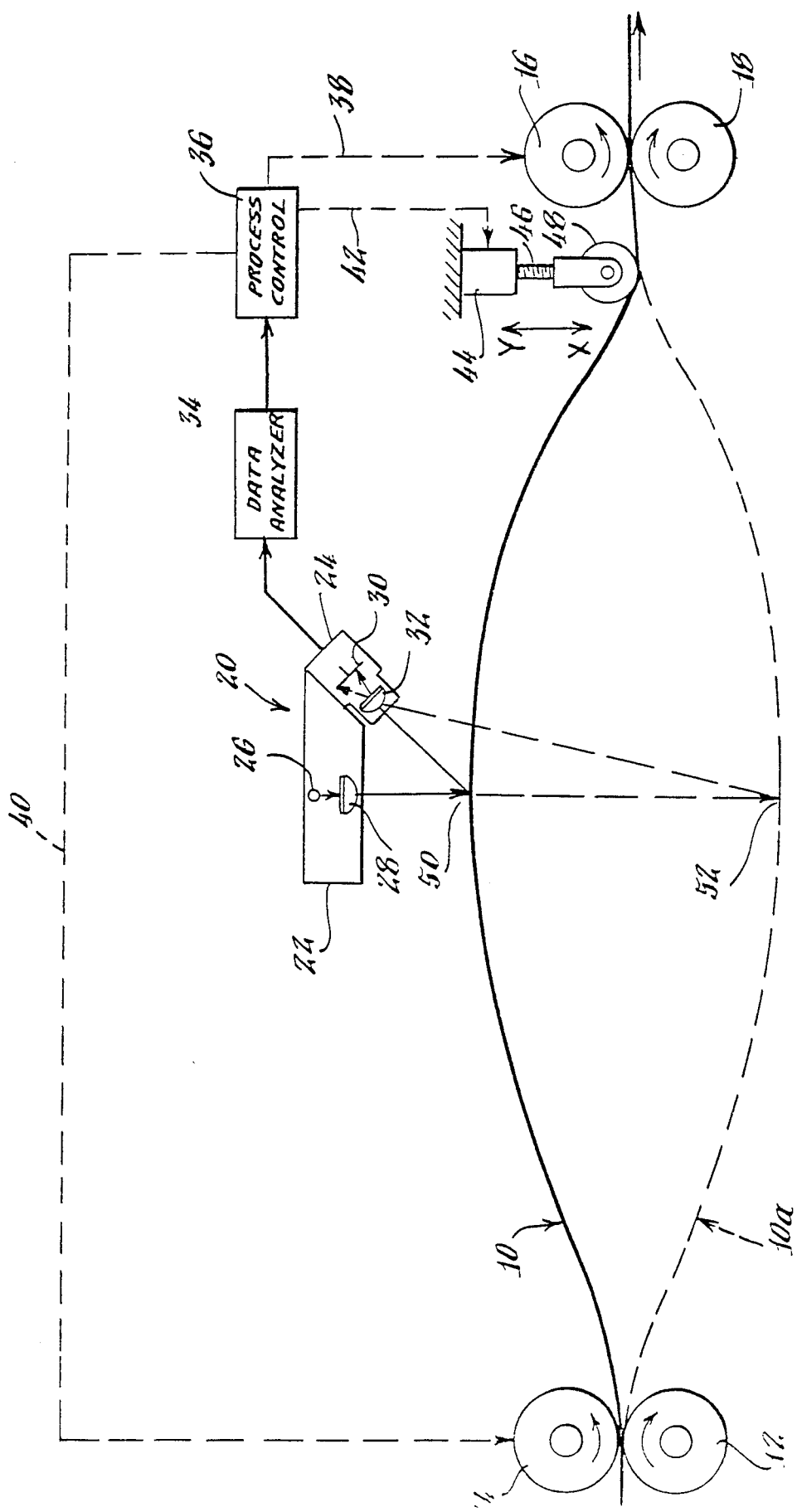

METHOD OF PAPER TENSION CONTROL TO MAINTAIN FLUTTER WITHIN A PREDETERMINED RANGE

This is a division of application Ser. No. 422,001 filed Sept. 23, 1982.

BACKGROUND OF THE INVENTION

The present invention relates to paper manufacturing and more particularly to an apparatus and method for sensing and controlling the tension of a paper web during the paper manufacturing process.

The tension in a web of paper as the paper is being manufactured is a critical parameter. The maintenance of proper paper sheet tension plays a major role, for example, in determining the "squareness" of the paper sheet. The squareness of paper is the ratio of the physical properties of the paper in the direction in which the paper travels through its manufacturing process to those properties in the direction substantially perpendicular to the direction of travel. Proper squareness is critical for many end uses of paper, such as xerography and other graphic applications. Paper sheet tension also has a major effect on the structure of the paper roll which is produced at the end of the paper manufacturing machine. Strict control of the structure of the paper roll is necessary to enable subsequent processing, for example on converting equipment such as rewinders and sheeters, to be accomplished.

Many grades of paper are very tension sensitive. Major product quality improvements would be possible through the measurement of actual sheet tension during the paper manufacturing process. To date, however, economical and reliable means for measuring such tension have been unavailable. Precise tension control is difficult in the absence of means for measuring the actual tension during the paper manufacturing process.

Tension control has previously been accomplished by controlling the relative speeds of the various independently driven sections of a paper machine. Unfortunately, this method of tension control can result in considerable variation in sheet tension due to changes in ambient environmental conditions, such as changes in humidity. Thus, while it is possible to control tension by varying the speed of travel at different points along a paper web, it is not always possible to maintain the tension without a means for continuously monitoring its value.

Past attempts to directly measure paper tension have involved the use of load cells which determine the load on the turning rolls in a paper manufacturing machine. This approach has not been found to be particularly useful on full size production machinery, however, because the mass of the required turning rolls acts to limit the system's sensitivity.

Accordingly, it would be advantageous to provide an apparatus and method for determining the sheet tension in a paper manufacturing machine in a dynamic manner. Accurate measurements of sheet tension could be used in conjunction with suitable data analysis and process control means to provide direct control of the sheet tension as paper is being manufactured. Such tension monitoring and control would yield considerable benefits in paper quality.

This invention relates to such an apparatus and method for tension measurement and control.

SUMMARY OF THE INVENTION

A paper manufacturing apparatus of the type comprising a plurality of rollers defining a paper path therebetween has means for driving at least one of the rollers to transport a paper web across the paper path. Non-contacting sensor means is provided. The sensor means is mounted adjacent a portion of the paper path for detecting, in a direction substantially perpendicular to the paper travel, variations in the position of a paper web travelling across the paper path. Means responsive to the sensor means is provided for controlling the tension in the paper web.

In one embodiment, the non-contacting sensor means comprises a light source aimed to project light toward the paper path, along with an optoelectronic detector positioned to detect the reflection of the projected light from the paper path. Radar or ultrasonic distance sensing apparatus could be used as alternate non-contacting sensor means.

Also provided is a method for controlling paper tension in a paper manufacturing apparatus. A paper web is driven across a paper path and the frequency and amplitude of flutter in the driven paper web is detected through the use of non-contacting sensor means. The tension in the paper web is adjusted to maintain the flutter within a predetermined range of frequency and amplitude.

BRIEF DESCRIPTION OF THE DRAWING

The FIGURE is a diagrammatic representation of a portion of a paper manufacturing machine embodying the present invention.

DETAILED DESCRIPTION OF THE INVENTION

Referring to the FIGURE, a paper web 10 is shown within a paper path defined by roller pairs 12, 14 and 16, 18. Rollers 12 and 18 can, for example, be idler rollers, in which case rollers 14 and 16 can be drive rollers. The drive apparatus, which drives rollers 14 and 16, is not shown. Such drive apparatus could consist of separate motors for each drive roller or an arrangement of a motor and mechanical drive system. The mechanical drive system could comprise gears, pulleys, chains or any combination thereof. Such drive systems for paper manufacturing machinery are well known in the art.

Within the paper path of a paper machine, the paper web 10 can undergo a phenomenon known as "flutter", wherein the paper web moves at a certain frequency and amplitude in a direction substantially perpendicular to the direction of travel of the paper web through the paper path. In the absence of flutter, paper web 10 would travel from roller pair 12, 14 to roller pair 16, 18 in a substantially straight line, with no curvature. When flutter occurs, paper web 10 will oscillate up and down, as shown in exaggerated fashion in the FIGURE. The amplitude of flutter is the total distance the paper web travels from the upper most position shown at 50 to the lower most position 52. In the FIGURE, the flutter of the paper web in the downward direction is represented by dashed line 10a.

The frequency of flutter is a measurement of the number times in which the paper web travels back and forth from its bottom most position 52 to its upper most position 50 within a given period of time. Such frequencies are typically measured in units of cycles per second, or "hertz".

It has been found that the amplitude and frequency of the flutter in a paper web travelling along a paper path can be used to determine the sheet tension in the paper. The flutter will increase in frequency and decrease in amplitude as the sheet tension increases. Conversely, as the sheet tension decreases, the flutter will increase in amplitude and decrease in frequency. In order to determine the amplitude and frequency of flutter, and thereby sheet tension, the present invention utilizes a noncontacting sensor means 20.

In a preferred embodiment, the noncontacting sensor means 20 comprises a light source 22 aimed to project light toward the paper path in which the paper web 10 is travelling. Light source 22 includes a light bulb or lamp 26 and a lens 28 mounted adjacent the paper path. The noncontacting sensor means 20 also includes an optoelectronic detector 24 which is positioned to detect light from light source 22 which has been reflected by paper web 10. Optoelectronic detector 24 includes a light sensor 30 and a lens 32.

As shown in the FIGURE, when paper web 10 is at its high point 50, light from light source 22 will be reflected by paper web 10 to one location on light sensor 30. When the paper web 10 is at its lowest position 52 as shown by dashed line 10a, light from source 22 will be reflected to a different position on light sensor 30. The magnitude of deflection of light across light sensor 30 can be used to determine the amplitude of paper flutter. The frequency of flutter can be determined by timing the amount of time it takes the reflected light beam to scan back and forth across light sensor 30.

The detected frequency and amplitude of the flutter can be advantageously used to maintain the tension in paper web 10 at a desired level. By continuously monitoring the flutter, the tension in the paper web can be adjusted to maintain the frequency and amplitude of the flutter within a predetermined range. By keeping the frequency and amplitude of the flutter within this predetermined range, the tension of paper web 10 will inherently be maintained as desired.

The output of optoelectronic detector 30 is coupled to a data analyzer 34, which analyzes the detector output to determine the frequency and amplitude of the paper flutter. Data analyzer 34 can comprise a conventional microprocessor or other central processing unit which is well known in the art. The output of data analyzer 34 is coupled to a process control unit which, in turn, is coupled to the paper manufacturing apparatus in order to control the tension of paper web 10.

Like analyzer 34, process control 36 can comprise electronic circuitry which is well known in the art. The output of process conrol 36 can control various machine functions in the paper manufacturing apparatus. For example, the velocity of drive roller 16 can be controlled by output line 38 of process control 36 to increase or decrease the tension on paper web 10. If, for example, drive roller 16 is controlled by an electric motor, the velocity thereof can be increased by increasing the voltage applied to the motor. By increasing the velocity of drive roller 16, without changing the velocity of drive roller 14, the tension on paper web 10 will be increased. Alternatively, the tension on paper web 10 may be decreased by decreasing the velocity of drive roller 16.

It would also be possible to control tension in paper web 10 by varying the velocity of drive roller 14. Thus, for example, process control unit 36 could send a signal through line 40 which would increase or decrease the velocity of a motor coupled to drive roller 14. If this velocity were increased, the tension in paper web 10 would decrease. If the velocity of drive roller 14 were decreased, the tension in paper web 10 would increase. Those skilled in the art will appreciate that the velocities of drive rollers 14 and 16 can be varied independently or together in order to control the tension in paper web 10.

An alternate method of controlling tension in paper web 10 would be to effectively increase the length of the paper path between roller pair 12, 14 and roller pair 16, 18. One such means for effectively increasing the paper path would be to provide an auxiliary roller 48 controlled through piston 46 of tension controller 44. Tension controller 44 could be either an electrically operated solenoid, an electro-hydraulic controlled unit, or any other reciprocating mechanical control means well known in the art. When auxiliary roller 48 is moved by tension controller 44 in the direction marked x, the effective length of the paper path will increase, and the tension on paper web 10 will increase. Conversely, when auxiliary roller 48 is moved in the direction marked y, the effective length of the paper path will be reduced, and the tension on paper web 10 will be reduced. Tension controller 44 is controlled by process control unit 36 through line 42. Process control output lines 38, 40 and 42 are shown as dashed lines because they are not all required. Any of the tension control means described herein, either alone or in combination, could be used to effect tension control on paper web 10. Those skilled in the art will appreciate that other tension control means may also be used without departing from the spirit and scope of the present invention, as set forth in the appended claims.

What is claimed is:

1. A method for controlling paper tension in a paper manufacturing apparatus comprising the steps of:
    driving a paper web across a paper path in said paper manufacturing apparatus;
    projecting an energy beam onto a surface of the web along a line which is substantially perpendicular to the web which energy beam is reflected by the web;
    detecting the energy beam reflected by the web with a noncontacting sensor to provide an indication of the spatial position of the web and enable measurement of the frequency and amplitude of flutter in said driven paper web; and
    adjusting the tension in said paper web in response to variations in the spatial position of the web, to maintain said flutter within a predetermined range of frequency and amplitude.

2. The method of claim 1 wherein said tension is adjusted by the additional step of:
    varying the velocity at which said paper web is driven at one end of said paper path.

3. The method of claim 1 wherein said paper web is supported by rollers at each end of said paper path and said tension is adjusted by the additional step of:
    varying the effective length of said paper path.

* * * * *